(12) United States Patent
Heleen

(10) Patent No.: US 6,444,237 B1
(45) Date of Patent: Sep. 3, 2002

(54) HERBAL COMPOSITION FOR ENHANCING SEXUAL RESPONSE

(76) Inventor: Pamela A. Heleen, P.O. Box 460463, San Francisco, CA (US) 94146

( * ) Notice: Subject to any disclaimer, the term of this patent is extended or adjusted under 35 U.S.C. 154(b) by 0 days.

(21) Appl. No.: 09/952,275

(22) Filed: Sep. 13, 2001

(51) Int. Cl.$^7$ .................. A01N 65/00; A61K 35/78; A61K 39/305
(52) U.S. Cl. ........................ 424/725; 424/752
(58) Field of Search .............. 424/195.1, 725, 424/752, 728, 777, 774

(56) References Cited

U.S. PATENT DOCUMENTS

| | | |
|---|---|---|
| 4,388,325 A | 6/1983 | Orzalesi |
| 5,880,124 A | 3/1999 | Gross |
| 6,007,824 A | 12/1999 | Duckett et al. |
| 6,100,287 A | 8/2000 | Stevens et al. |
| 6,117,872 A | 9/2000 | Maxwell et al. |
| 6,165,975 A | 12/2000 | Adams et al. |
| 6,172,060 B1 | 1/2001 | Garvey et al. |
| 6,207,713 B1 | 3/2001 | Fossel |
| 6,232,321 B1 | 5/2001 | Garvey et al. |
| 6,274,557 B1 | 8/2001 | Silverman et al. |
| 6,274,581 B1 | 8/2001 | Gross |
| 6,277,884 B1 | 8/2001 | de Tejada |

*Primary Examiner*—Christopher R. Tate
*Assistant Examiner*—Patricia Patten
(74) *Attorney, Agent, or Firm*—Cohen & Grigsby, P.C.

(57) ABSTRACT

The present invention provides a unique combination of herbal ingredients designed to overcome natural inhibitors of human sexual response and allow for improved response and psychological effects. The composition is comprised of extracts taken from crataegus monogyna berry, turnera diffusa, pfaffia paniculata, ginkgo biloba, pygeum africanum, and ginsenosides extract, that are combined with L-arginine, L-glutamic acid and L-theanine in amounts effective to produce desired results.

15 Claims, No Drawings

HERBAL COMPOSITION FOR ENHANCING SEXUAL RESPONSE

FIELD OF INVENTION

The present invention relates to compositions of herbal ingredients and, more particularly, to herbal compositions and methods which can be used for enhancing human sexual response.

BACKGROUND OF THE INVENTION

The first major scientific breakthrough in the area of enhanced human sexual response in recent years has been attributed to researchers at Vanderbilt University in Nashville, Tenn. who discovered the important role that cyclic guanosine monophosphate nucleotide ("cyclic-GMP") plays in the occurrence of an erection in humans. For a clitoral or penile erection to occur this "pro-erection" chemical cyclic-GMP must be present in a sufficient quantity so that it can overcome an antagonist enzyme, phosphodiesterase type 5 ("PDE-5") and produce an erection. This antagonist enzyme rapidly breaks down cyclic-GMP, thus hindering the sexual response.

Furthering this research, in 1998, the Nobel Prize in Medicine or Physiology was awarded to American researchers who recognized nitric oxide as a signaling molecule in the cardiovascular system, including its role in vaso-dilation and the production and release of cyclic-GMP. Sufficient quantities of nitric oxide (NO) must be present for the cyclic-GMP to promote sexual response. Generally, when there is more cyclic-GMP in the penis/clitoris than there is PDE-5, and nitric oxide is present in sufficient quantities, an erection/distension may occur with sufficient stimulation.

Subsequently, it was recognized that the amino acid, arginine, plays an important role as a biochemical precursor to nitric oxide. Recently, researchers at the University of Pennsylvania, discovered the enzyme, arginase, which breaks down the body's stores of arginine without producing NO. The researchers also discovered an agent, S-(2-boronoethyl)-L-cysteine ("BEC"), which binds to arginase preventing it from destroying the body's arginine. This discovery reconfirmed the role of arginine as a biochemical precursor to nitric oxide, and its importance in sexual function. As with most biochemical reactions, approaching either side of the equation produces equivalent (desirable) results. In other words, the arginase can be reduced or arginine can be supplemented. If arginine is supplemented in significant enough amounts to "flood" past, or use up the body's arginase (and still be present in significant amounts), then the desired results are achieved. Thus, for many people, the cause of erectile dysfunction is insufficient arginine (or an over abundance of arginase). Management of this deficiency helps to address sexual dysfunction.

At present, there are a number of products produced and made available to consumers desiring to improve or enhance their sexual performance. Generally, these products can be divided into two categories. The first category includes those products which contain "old school" or traditional herbal ingredients. Typically, these products rely on yohimbe or muira puama. Such herbal preparations provide only a marginal value to a limited population. Their mechanism of action, if any, is unknown. The second category includes pharmaceutical products which address the physiology of sexual response at the Cyclic GMP/PDE-5 level.

For instance, a major pharmaceutical company produces sildenafil (also known as Viagra™) that functions by blocking PDE-5 enzyme thus inhibiting its antagonistic action. The result is to provide a relative increase in chemical balance favoring cyclic-GMP. When cyclic-GMP is present in a higher proportion than its antagonist enzyme PDE-5, blood enters the sexual organs more easily. When nitric oxide is released upon sufficient sexual arousal, the penile artery dilates, the penis becomes engorged with blood and the force of turgor causes it to stiffen. When the penile artery is dilated, the veins that draw blood away are pinched shut, otherwise blood would leave just as quickly as it enters and turgor would not build. A comparable process occurs in females.

However, sildenafil and other pharmaceutical products are known to have some unfortunate side-effects, including headaches, nasal congestion, flushing and the infamous blue-tinted vision. In most cases, currently available products must be ingested one to several hours prior to desired effects, thus impeding spontaneity. Furthermore, approximately 30% of men and an even greater percentage of women with sexual dysfunction do not respond to products that function by blocking PDE-5 (such as sildenafil). This lack of response could be attributed to the timing of the sildenafil mechanism, in that the PDE-5 inhibition occurs after the arginase has degraded the system's supply of arginine and before NO is produced from the arginine. A system deprived of sufficient arginine cannot achieve sexual response.

Another natural/herbal product sought to address this deficiency by including L-arginine in combination with natural ingredients, such as ginseng and zizyphi fructus. However, based upon research and reported usage, the product did not consistently provide improved response. When beneficial response was reported, it generally did not appear until after 10 days to two weeks of administering the product daily. Generally, they failed to recognize the importance of ingesting large amounts of arginine to flood and overwhelm arginase. Despite the research and existence of arginine-bearing products, none have yet to appreciate the ability of arginine to provide significant synergistic effect when used in combination with ginseng and theanine.

Ginseng, specifically ginsenoside Rg1 and Rg3, is a NO synthase catalyst which acts to enhance the production of NO significantly. Theanine, a fast acting vasodilator, allows all the ingredients to assimilate into the body at a much greater speed. Both mechanisms serve to cause the flooding action to overwhelm the arginase.

Thus, there is a need for an improved product and method which are capable of enhancing sexual response and vitality without the disadvantages of the prior art products and methods. It is also desirable to provide a product and method that are effective, convenient and economical. It is further desirable to provide consumers with an effective natural/herbal alternative to current synthetic products. Another objective is to provide such a product that works equally as well for both men and women.

SUMMARY OF THE INVENTION

The present invention provides a unique combination of natural/herbal ingredients designed to inhibit arginase and stimulate sufficient release of nitric oxide to produce sustained, improved sexual response and psychological effects. The composition is comprised of extracts taken from crataegus monogyna (hawthorn) berry, turnera diffusa (damiana), pfaffia paniculata (suma), ginkgo biloba, pygeum africanum, and ginsenosides (panax ginseng extract), that are combined with L-arginine, L-glutamic acid and L-theanine in amounts effective to produce desired results.

This composition uniquely combines an array of herbal derivatives that have been shown to have a beneficial effect.

Ginsenoside, particularly Rg1 and Rg3, and glutamic acid are mediators of nitric oxide release. They facilitate the release of the nitric oxide from the arginine. Crataegus monogyna, and ginkgo biloba are vaso-dilating. Crataegus monogyna and ginkgo biloba also inhibit blood platelet aggregation; thereby improving blood flow. They each contribute directly to more turgid erections/clitoral distensions since vascular insufficiency is a common mechanical deficit leading to erectile dysfunction. Pygeum africanum provides relief from benign prostatic hyperplasia (swollen prostate), often a cause of or a contributor to, erectile dysfunction in itself. Damiana and suma are traditional herbal sexual enhancements which have been shown to be effective in animal studies. The percentage achieving ejaculation is increased. and the intercopulatory interval is shortened with these components.

In a preferred embodiment of the present invention the composition further includes effective amounts of BEC and Lepidium meyenii ("Maca"), a traditional Peruvian aphrodisiac. Additionally, Maca has been shown to improve sexual response in rats substantiating long held claims to its traditional use. BEC has been found to bind to and inhibit arginase, the enzyme that digests arginine before it can be used to produce nitric oxide. BEC and Maca together provide an effective enhancement to this formula.

The present composition is comprised of herbal powder extracts. The extracts as used herein are concentrate of water-soluble and or alcohol-soluble plant components. They are mixed together using a conventional process to form a powder composition. Preferably, a flavor extract or component is added to the composition to give it a pleasant taste. The amount of flavor extract varies depending upon its concentration and the strength or type of flavor desired for the drink. In a preferred embodiment, the flavor extract comprises about 70–90% of the total weight of the powder combination and may include natural and/or artificial flavoring, coloring, and sweeteners.

The herbal composition of the present invention is administered orally and can be provided in any conventional form such as powders, granules, or food or beverage additives. In a preferred embodiment of the present invention, the composition is presented as a dry product for reconstitution with water or other suitable medium. Preferably, it is formulated as a highly absorbable (bio-available) mix-with-water drink for daily consumption. While water is the preferred medium, other liquids (such as grape juice) may also be used. Effective media is that which would not disturb the synergy created among the particular components of the mix. Preferably the composition is formulated into unit dosages. A unit dosage can comprise an effective amount of the product for consumption only once a day to ensure consumer ease of use and, ultimately, compliance with the recommended intake amount. It is expected that consistent daily administration of the present composition will allow for spontaneous reaction to a sexual event.

Other features, aspects and advantages of the present invention will become better understood or apparent from a perusal of the following detailed description of the invention and appended claims.

DETAILED DESCRIPTION OF THE INVENTION

An important aspect of the present invention includes a novel inhibitor of enzymes that obstruct spontaneous sexual response. The present invention provides a unique combination of ingredients designed to overcome inhibitors of sexual response, such as arginase, and thus provides improved sexual response and psychological effects. The composition is comprised of extracts taken from crataegus monogyna (hawthorn) berry, turnera diffusa (damiana), pfaffia paniculata (suma), ginkgo biloba, pygeum africanum, and ginsenosides (panax ginseng extract), that are combined with L-arginine, L-glutamic acid and L-theanine in amounts effective to produce desired results. This composition uniquely combines an array of herbal derivatives that have been shown to have a beneficial effect. It is contemplated that the composition will provide an effective amount of arginine in combination with theanine to provide a unique synergistic effect and, in essence, overwhelm levels of arginase to lead to enhanced sexual response. Preferably, the synergy of this composition is further enhanced by the addition of BEC. The use of theanine in combination with BEC and arginine would never be obvious since theanine is known as a calming agent in green tea which counters the high levels of caffeine in green tea. In the present application, theanine is found to produce an unexpected benefit, exhibited by a warming sensation due to its vasodilatory property. This feeling can have a favorable psychological effect in addition to the favorable dilation of the penile or clitoral artery. This ingredient in combination with the present composition surprisingly acted as a sexual stimulant. The three-fold attack on the problem—namely flooding the system with L-arginine in one dose, inhibiting the antagonist arginase with BEC, and quickly dilating the blood vessels with theanine —is a new and unique approach to sexual response enhancement. The use of a one-a-day packet of ingredients allows for true spontaneity in that the user is physiologically able to respond at any time. The user does not have to plan a sexual event around advance administration of the composition.

This composition uniquely combines an entire array of herbal derivatives that have been shown to have a beneficial effect. It allows for the highest potency of arginine per unit of any product available today. The composition is not merely a mixture of constituents but provides a new composition of ingredients that have a synergistic effect. Because the components in the composition are from natural sources, all of which have been shown to be relatively safe, the present composition provides a safer product for daily use without all of the adverse effects associated with the current commercial products. Further, it works equally as well for both men and women.

For purposes herein, the term "about" means plus or minus ten percent of the number at issue.

The following examples of the composition follow the teachings of and illustrate the present invention:

EXAMPLE 1

An herbal product preferably containing the following composition:

| Component | Weight in grams |
| --- | --- |
| L-Arginine | 1.5 g |
| L-Glutamic acid | .15 g |
| Crataegus monogyna berry extract | .08 g |
| Turnera diffusa extract | .07 g |

-continued

| Component | Weight in grams |
|---|---|
| Pfaffia paniculata extract | .07 g |
| Ginkgo biloba extract | .06 g |
| Pygeum africanum extract | .05 g |
| L-Theanine | .04 g |
| Ginsenosides extract | .02 g |

The powder components were combined using conventional methods. A flavoring component was added to the combination. Appropriate amounts of the powder were measured and divided, and packaged into single serving packets. Each single packet comprised a total weight of about 15 grams of "active" ingredients and flavoring component. However, the weight of the packet may vary depending upon the desired dosage.

The composition was mixed with water and ingested by different persons participating in a pilot study. The composition was very effective. A majority of participants reported more pronounced sexual response in direct comparison to the leading herbal "Sexual Performance Enhancer".

EXAMPLE 2

An herbal product preferably containing the following composition:

| Component | Weight in grams |
|---|---|
| L-Arginine | 3.0 g |
| L-Glutamic acid | .30 g |
| Crataegus monogyna berry extract. 7:1 | .16 g |
| Turnera diffusa extract 4:1 | .14 g |
| Pfaffia paniculata extract | .14 g |
| Ginkgo biloba extract | .12 g |
| Pygeum africanum extract | .10 g |
| L-Theanine | .08 g |
| Ginsenosides extract | .04 g |

Based upon clinical findings and background research, this composition is expected to yield desired beneficial effects.

EXAMPLE 3

An herbal product preferably containing the following composition:

| Component | Weight in grams |
|---|---|
| L-Arginine | 1.5 g |
| L-Glutamic acid | .15 g |
| Crataegus monogyna berry extract | .08 g |
| Turnera diffusa extract | .07 g |
| Pfaffia paniculata extract | .07 g |
| Ginkgo biloba extract | .06 g |
| Pygeum africanum extract | .05 g |
| L-Theanine | .04 g |
| Ginsenosides extract | .02 g |
| BEC | .25 g |

The composition also includes the ingredient BEC. Based upon clinical findings and background research, the addition of BEC to the composition is expected to yield even more pronounced sexual response.

While the foregoing has been set forth in considerable detail, the compositions and methods are presented for elucidation and not limitation. It will be appreciated from the specification that various modifications of the invention and combinations of elements, variations, equivalents, or improvements therein may be made by those skilled in the art, and are still within the scope of the invention as defined in the appended claims.

What is claimed is:

1. An orally administered composition of ingredients for enhancing sexual response comprising at least about 1.5 grams of L-arginine, at least about 0.04 grams of L-theanine, and effective amounts of each of the following: L-glutamic acid, crataegus monogyna berry extract, turnera diffusa extract, pfaffia paniculata extract, ginkgo biloba extract, pygeum africanum extract, and ginsenoside, wherein said extracts include concentrates of water-soluble or alcohol-soluble plant components.

2. A composition as set forth in claim 1 further including S-(2-boronoethyl)-L-cysteine.

3. A composition as set forth in claim 1 wherein said ginsenoside is selected from the group consisting of ginsenoside Rg1, ginsenoside Rg3 and combinations thereof.

4. A composition as set forth in claim 1 further including a flavoring component.

5. A composition for enhancing sexual response as set forth in claim 1 made by: (a) combining said L-arginine, L-glutamic acid, crataegus monogyna berry extract, turnera diffusa extract, pfaffia paniculata extract, ginkgo biloba extract, pygeum africanum extract, L-theanine, ginsenosides and flavoring component into a powder combination, (b) measuring a unit dosage of said powder combination, and (c) combining said powder combination with a liquid.

6. A method of enhancing an individual's sexual response as set forth in claim 1, wherein said beverage is administered daily in an amount between about 1.5 grams and about 2.1 grams of said composition.

7. An orally administered composition of ingredients for enhancing sexual response comprising L-arginine in a range of about 1.5 g to about 3.0 g, L-theanine in a range of about 0.04 g to about 0.08 g, L-glutamic acid in a range of about 0.15 g to about 0.30 g, crataegus monogyna berry extract in a range of about 0.08 g to about 16 g, turnera diffusa extract in a range of about 0.07 g to about 0.14 g, pfaffia paniculata extract in a range of about 0.07 g to about 0.14 g, ginkgo biloba extract in a range of about 0.06 g to about 0.12 g, pygeum africanum extract in a range of about 0.05 g to about 0.10 g, and ginsenosides in a range of about 0.02 g to about 0.04 g, wherein said extracts include concentrates of water-soluble or alcohol-soluble plant components.

8. A composition as set forth in claim 7, further including BEC.

9. A composition as set forth in claim 7, wherein said BEC is in a range of about 0.020 g to about 1.0 g.

10. A composition as set forth in claim 7, wherein said ginsenoside is selected from the group consisting of ginsenoside Rg1, ginsenoside Rg3 and combinations thereof.

11. A composition as set forth in claim 7 further including a flavoring component.

12. A composition as set forth in claim 11, wherein said flavoring component is in the range of about 12 grams to 16 grams.

13. A method of enhancing an individual's sexual response as set forth in claim 12, wherein said beverage is administered daily in an amount between about 1.5 grams and about 2.1 grams of said composition.

14. A method of enhancing an individual's sexual response comprising orally administering an effective amount of a composition according to claims 1 or 6.

15. An orally administered composition of ingredients for enhancing sexual response comprising at least about 1.5 g of L-arginine, at least about 0.04 g of L-theanine, at least about 0.15 g of L-glutamic acid, at least about 0.08 g of crataegus monogyna berry extract, at least about 0.07 g of tumera diffusa, at least about 0.07 g of pfaffia paniculata extract, at least about 0.06 g of ginkgo biloba extract, at least about 0.05 g pygeum africanum extract, and at least about 0.02 g of ginsenosides, wherein said extracts are concentrates of water-soluble or alcohol-soluble plant components.

* * * * *